United States Patent [19]

Cook

[11] 4,319,975

[45] Mar. 16, 1982

[54] DERIVATIZED AGAROSE AND METHOD OF MAKING AND USING SAME

[75] Inventor: Richard B. Cook, Rockland, Me.

[73] Assignee: FMC Corporation, Philadelphia, Pa.

[21] Appl. No.: 198,372

[22] Filed: Oct. 20, 1980

[51] Int. Cl.$^3$ .................. G01N 27/26; G01N 33/16
[52] U.S. Cl. .................. 204/180 G; 204/299 R; 252/315; 252/316; 536/2; 536/52
[58] Field of Search .................. 204/180 G, 299 R; 252/315, 316; 536/2, 52; 195/69

[56] References Cited

U.S. PATENT DOCUMENTS

| | | | |
|---|---|---|---|
| 3,527,712 | 9/1970 | Renn et al. | 204/180 G X |
| 3,956,272 | 5/1976 | Tixier | 536/2 X |
| 3,956,273 | 5/1976 | Guiseley | 536/2 X |
| 3,959,251 | 5/1976 | Porath et al. | 536/2 X |
| 4,055,510 | 10/1977 | Peska et al. | 252/426 |

OTHER PUBLICATIONS

Smithies, O., Biochemical Journal, vol. 61, p. 629 (1955), An Improved Procedure for Starch-gel Electrophoresis: Further Variations in the Serum Proteins of Normal Individuals.
Peacock, et al., Biochemistry Journal, vol. 7, pp. 668–674 (1968), Molecular Weight Estimation and Separation of Ribonucleic Acid by Electrophoresis in Agarose–Acrylamide Composite Gels.
Bode, H., Analytical Biochemistry, vol. 83, pp. 204–210 (1977), The Use of Liquid Polyacrylamide in Electrophoresis.
Baumann and Chrambach, Analytical Biochemistry, vol. 70, pp. 32–37, (1976), A Highly Crosslinked, Transparent Polyacrylamide Gel with Improved Mechanical Stability for Use in Isoelectric Focusing and Isotachophoresis.
Brown, et al., Electrophoresis '79, p. 235, Ed. B, Berlin (1980), Soluble Polyacrylamide Gradient Gels in the Separation and Estimation of Proteins.
Lowe, C., Int. J. Biochemistry, vol. 8, pp. 177–181 (1977), Affinity Chromatography: The Current Status.
Sargent, J. R., Methods in Zone Electrophoresis, p. 75.
Ashton, G., Nature, vol. 180, pp. 917–919 (1957), Serum Protein Differences in Cattle by Starch Gel Electrophoresis.
BioRad 1980 Catalog, p. 37, BioRad Laboratories.
Dea, Moorhouse & Rees, J. Molecular Biology, vol. 90, pp. 269–284 (1974), The Agarose Double Helix and Its Function in Agarose Gel Structure.
Deuel, et al., Advan. Chem. Series, p. 51, Some Properties of Locust Bean Gum.
Pharmacia Fine Chemicals AB, Uppsala, Sweden, pp. 8–11, Sephadex Properties.
Gupta, et al., Journal of Chromatography, vol. 169, pp. 183–190 (1979), Gel Filtration Medium Derived from Guar Gum.

*Primary Examiner*—Arthur C. Prescott
*Attorney, Agent, or Firm*—Robert D. Jackson; Eugene G. Seems

[57] ABSTRACT

Derivatized agarose is produced by introducing into the disaccharide unit of the agarose polymer chain, at least one substituent having a molecular weight range greater than 100 to about 1,000,000. The derivatized agarose is useful as a sieving gel in electrophoresis and diffusive interactions.

12 Claims, No Drawings

DERIVATIZED AGAROSE AND METHOD OF MAKING AND USING SAME

This invention relates to derivatized agarose, particularly to derivatized agarose having new and novel uses in electrophoresis and diffusive interactions.

In the electrophoresis art it is known to use sieving gels for the separation of biological substances. Such gels are characterized by the presence of a microporous structure which exerts a selective action on the migrating fractions, restricting passage of the high molecular weight fractions while permitting passage of the low molecular weight fractions. The technique was originally carried out using starch as the sieving gel; Smithies, O., Biochem, J. 61,629 (1955). However, starch gels suffers from several disadvantages; 1. they are not clear; 2. they are discontinuous and therefore cannot be dried and preserved intact; 3. their dimensional strength is low; 4. their range of porosities is limited; 5. proteins separated in them are recovered in poor yields and as recovered contain low M.W. starch contaminants. Later, polyacrylamide was developed as an electrophoretic gel sieving medium. A "stacking gel" variation was subsequently devised and this led to disc electrophoresis as a popular gel sieving tool.

Polyacrylamide forms exceptionally clear, typically continuous gels which can be dried and stored without fracturing. They can be prepared in a wide range of concentrations and consequent porosities.

Although an advance over the earlier starch gels, polyacrylamide gels were not entirely satisfactory and exhibited several major disadvantages. For instance, the acrylamide monomer used to form the polyacrylamide is a cumulative neurotoxin and varying amounts remain in the polymerized gels depending on the conditions of polymerization thereby creating a health hazard. The conditions of polymerization can also affect gel porosity and the tendency of these gels to swell differently in different aqueous solutions. This has limited the reproducibility of these gels and thus curtailed their widespread use. Moreover, polyacrylamide gels notoriously have low gel strength, particularly at low concentrations. Furthermore, such gels are difficult to destain and use as a preparative gel medium because of their retentiveness and lack of freeze-thaw characteristics.

The many advantages and uses of sieving gels has provided a strong incentive to develop new and improved types. Although numerous publications have appeared on this subject, none have described convenient methods which are nondenaturing to the proteins separated and are also amenable to the range of conditions (urea, SDS, triton, etc.) which are commonly used in such separation techniques.

To overcome the dimensional strength liability of low concentration polyacrylamide gels, it has been proposed to incorporate agarose into the gel; Peacock, A. et al., Biochemistry 7,668 (1968). A similar approach was taken by Bode, Anal. Biochemistry 83,204 (1977) who incorporated liquid polyacrylamide into agar gels but found that the practical upper limit for such formulations was only 5%. In Anal. Biochemistry 70,32 (1976) by Chrambach, A. et al., there is disclosed the use of diallyltartardiimide (DATD) instead of disacrylamide as a means of increasing adhesion and therefore mechanical stability of the polyacrylamide gels in glass tubes. This system also facilitates resolubilization of the gels by oxidative hydrolysis although it tends to degrade proteins.

Similarly, attempts to recover proteins separated in polyacrylamide by swelling the gel with quaternary ammonium compounds or dissolving them in $H_2O_2$ also risk danger to the proteins and the researcher isolating them; Peacock, A. and Dingman, C., Biochemistry 7,668 (1968).

As a means of overcoming the difficult protein recovery characteristics of polyacrylamide gel for preparative applications, there is described by Brown, M. et al., Electrophoresis '79, page 235, Ed. B. Radola, Walter DeGruyter, Berlin (1980) a method of cross-linking which could be reversed by treatment with 1 M NaOH. However, such harsh conditions risked destroying the very protein samples which were being analyzed.

The attempts to combine agarose and polyacrylamide, Brown, M., et al., Electrophoresis '79, page 235, Ed. B. Radola, Walter DeGruyter, Berlin (1980) and Lowe, C., Int. J. Biochemistry, 8,177 (1977) were based on the recognition that these two gel media had almost opposite characteristics: whereas agarose has a high gel strength at low concentrations, polyacrylamide has a low gel strength at low $\leq 7\%$ concentrations. Whereas agarose gels typically exhibit a slight translucence, polyacrylamide gels in many formulations are crystal clear; whereas agarose exhibits very little sieving toward most serum proteins 50,000–500,000 MW polyacrylamide gels are the medium of choice for proteins within this range of molecular weights, Sargent, J. R. in "Methods in Zone Electrophoresis," page 75, pub by BDH Ltd, Poole, England, 2nd Ed. (1969). In practice, however, the composite gel approach met with only limited success. The traditional application of these two media employs agarose for the sieving separation of proteins >500,000 MW. While those <500,000 (MW) daltons are best resolved in polyacrylamide gels which can readily be formed so as to have exclusion limits <2,000 (MW) daltons, Ashton, G., Nature, 180,917 (1957) and BioRad 1980 Catalog, Page 36, BioRad Laboratories, Richmond, Calif. The approach of "filling" with polyacrylamide the large, highly porous agarose gels whose ultrastructure has been reported in detail by Rees, et al., J. Molecular Biology 90,269 (1974) therefore ultimately proved to be a mediocre remedy and compromised some of the best properties of each medium.

Another approach to the development of sieving media for both electrophoretic and chromatographic applications has been to cross-link otherwise nongelling, neutral polysaccharides under appropriate concentration conditions. Examples of such cross-linked sieving media are: locust bean gum, Duel, H. and Neukon, H., Advan. Chem. Ser., No. 11,51 (1954) Dextran, Flodin, P., Dextran gels and their applications in gel filtration, Pharmacia, Uppsala, Sweden (1962) Guar gum, Gupta, K., Sahni, M. et al., J. Chromatography 169,183 (1979), and cellulose, Peska, J. and Stamberg, J., U.S. Pat. No. 4,055,510 (Oct. 25, 1977). The principal disadvantages of such procedures are: that the gels cannot be readily dissolved after cross-linking for preparative protein recovery applications, and the gels cannot be readily polymerized in the presence of the necessary buffers or ampholytes required for most electrophoretic separation techniques.

A modified agarose is described in U.S. Pat. No. 3,956,273 to Guiseley. The product is prepared by introducing certain substituents into the disaccharide molecule, which is the principal component of agarose, the degree of substitution being from about 0.01 to 1.0. Such substituents are lower aliphatic hydrocarbon, lower hydroxyhydrocarbon, and acyl radicals, the molecular weight of the substituent having an upper limit of about 100. Such modified agarose gels exhibits low gelling and and melting temperatures; gel clarity is also increased. The Guiseley patent does not mention anything about the porosity of such modified agarose or whether it has sieving properties.

It has now been discovered that agarose, which has been derivatized, is an effective sieving gel medium and the use of such gel for the resolution and separation of biological substances by electrophoretic means constitutes an object of the invention. Another object of the invention is to provide derivatized agarose compositions having restricted pore size and exhibiting sieving gel properties. Other objects and purposes will become manifest subsequently herein.

In accordance with the invention, there is provided a derivatized agarose, useful as an electrophoretic sieving gel, containing at least one substituent having a molecular weight greater than 100 to about 1,000,000 and a conformational shape such that the average pore diameter of the derivatized agarose is not reduced below about $10°$ A units, the degree of substitution (D.S.) being greater than about 0.001 and no more than about 2.0. So far as can be ascertained, the presence of the substituent sterically inhibits helix and junction zone formation and it is this effect which accounts for the sieving properties of the herein derivatized agarose. Generally speaking, the introduction of any substituent on the agarose imparts some degree of sieving action, although the effect would be minimal where the substituent has small molecular bulk. Where the substituent is a high molecular weight moiety, it may restrict access to the agarose pores, in addition to inhibiting helix and junction zone formation. Depending more or less on their conformational shape, such bulky moieties can block or even close off the pores of the agarose thereby destroying its sieving properties.

Substituents can also be selected which impart affinity, hydrophobic or ion exchange properties, in addition to the required steric configuration, thereby providing for separations based on both molecular size and one or more of the aforesaid properties. The following are illustrations of these features:

(1) Where the agarose derivative has a negative charge under alkaline buffer conditions (i.e. such as a carboxylate or sulfate anion) this will increase the cathodal flow of water under gel electrophoresis conditions resulting in a cathodal displacement of the sieved proteins by comparison to a neutral substituent analog. It will also result in a separation in which the mobility of extremely basic proteins is retarded.

(2) Where the agarose derivative has a positive charge under the electrophoresis buffer conditions, then this will result in an anodal flow of water in the gel, thereby resulting in a sieving separation which is anodally displaced by comparison to a neutral substituent analog. It will also result in a separation in which the mobility of extremely acidic proteins is retarded.

(3) Where the agarose derivative consists of extended (>2 carbons) alkyl or aromatic structures which exhibit hydrophobic interactions with proteins, then the separations obtained will be a function of both the sieving effects of the matrix and the lipophilicity of the proteins being separated.

(4) Where the agarose derivative exhibits a biological affinity for the proteins or other substances being separated, then the separation obtained will be a function of the combined sieving and affinity effects exerted by the matrix.

In all cases, the substituent chosen must be sufficiently stable to the effects of heating ($\leq 80°$ C.) in the presence of typical electrophoresis buffers (pH 5-9) and not more than 50% of the derivative should be lost during a typical dissolution of the agarose derivative and subsequent gel formation (typically $\leq 15$ minutes).

The extent of substitution can be defined in terms of the four theoretically available sites for reaction which are present in the disaccharide molecule composed of D-galactose and 3,6-anhydro-L-galactose, which disaccharide is the principal structural unit of agarose. On this basis, a product wherein all of the available sites are completely reacted has a degree of substitution (D.S.) of 4.0. As previously pointed out, the herein derivatized agarose has a D.S. of from about 0.001 to about 2.0. In general, the D.S. is not greater than that required to achieve the requisite reduction in pore size.

Derivatized agarose compositions exhibiting sieving properties in accordance with the invention are prepared using the known synthetic procedures for introducing substituents into the agarose disaccharide chain. These include one-step reactions as exemplified by the Williamson ether synthesis, graft-polymer free radical reactions and bifunctional reagent reactions which minimize cross-linking. Thus, agarose is first dissolved in a strong alkaline, preferably aqueous solution such as 0.5 to 1.5 molar alkali metal hydroxide after which a suitable reagent is added, such as dimethyl sulfate, ethyl bromide, 1-bromopropane, 2-bromopropane, 3-bromopropene, propylene oxide, ethylene oxide, 2-chlorethanol, epichlorohydrin, butylene oxide, diepoxybutane, and the like. Since some discoloration or darkening of the solution tends to occur during the reaction when it is carried out in aqueous alkaline solution, producing a product which is discolored although otherwise entirely satisfactory, it is also preferred to block the aldehyde end group of the agarose, for example by reduction, before bringing the agar or agarose into contact with aqueous alkali, thus preventing the color-forming reaction which involves the aldehyde group from taking place. The blocking agent of choice is a borohydride, particularly an alkali metal borohydride such as sodium borohydride, which reduces the aldehyde end group to an alcohol (hydroxy) group.

A difunctional reagent such as epichlorohydrin which is capable of producing cross-linking under appropriate conditions to form a water-insoluble product can be used only under conditions which prevent cross-linking and which result in a watersoluble product, i.e., soluble to the extent of at least 2% by weight at 90° C. As is well known, cross-linking can be avoided by employing a dilute (less than about 3.5% by weight) solution of agar or agarose for the reaction and by other techniques well known to those skilled in the art. Except for the necessity of of avoiding formation of a water-insoluble product when difunctional reagents are used, there is nothing critical about the concentrations or other conditions employed.

The reaction is preferably carried out at an elevated temperature from about 70° to 100° C., or more, but lower temperatures may be used to minimize discoloration if the aldehyde end group is not blocked or to reduce loss when a relatively volatile reagent is used. At lower temperatures the reaction is slower and in some cases the selected reagent is decomposed by reaction with the water before the desired extent of reaction with agarose can be achieved.

After completion of the reaction, the mixture is cooled to 50°–60° C. (if it is at a higher temperature), the alkali is neutralized with an acid or is removed by dialysis or other conventional procedure, and the product is purified by conventional procedures. For example, the solution may be gelled by cooling, frozen and allowed to thaw, then washed and dried; or the product may be precipitated from the reaction solution by mixing with it a water-miscible organic liquid which is a non-solvent for the product, such as methanol, ethanol, filtered, washed with the non-solvent and dried.

The process of the present invention can also be carried out in an organic solvent such as N,N-dimethylformamide, pyridine, or similar solvents; indeed, reaction in such a solvent is preferred by acylation, e.g., with acetyl chloride or propionyl chloride. Under these conditions, blocking of the aldehyde end group is usually unnecessary, little or no discoloration occurring during the reaction. In addition, acid anhydrides can be employed for acylation instead of acyl halides if desired.

The precise amount of alkylating, alkenylating, acylating or hydroxyalkylating agent employed depends upon the conditions of the reaction and the extent of substitution (D.S.) desired. Usually a large excess above the amount theoretically necessary is used because of the tendency of the agent to react to some extent with water, when present.

A derivatized agarose herein having 4.0% by weight of hydroxyethyl as the substituent has an average pore diameter of 69±22 MU while 9.0% hydroxyethyl further reduces pore diameter to 42±18 MU; non-derivatized agarose typically has a pore diameter of 106±52 MU.

Derivatized agarose of the invention can also be produced by graft copolymerization with various ethylenically unsaturated monomers such as acrylonitrile, acrylamide, $\alpha_1 \beta$ unsaturated carboxylic acids and the like. This procedure is useful for introducing high molecular weight substituents into the agarose molecule.

High molecular weight, multifunctional substituents may be formed on the agarose by means of sequential reactions which join together their low molecular weight intermediates. This approach avoids the solubility and reactivity limitations of the high M.W. substituent if attempted in a one-step reaction. Such reactions involve formation of a reactive intermediate with the agarose followed by subsequent coupling with a mono or bifunctional amine, aminoalcohol, thiol, or dithiol. In a third step, it is possible to form amide linkages or otherwise substitute the available amine or thiol moieties with other alkyl or aromatic groups thereby building up the size of the overall substituent. In the initial matrix activation step, bifunctional reagents such as cynogen bromide, cyanuric chloride, divinyl sulfone, epichlorhydrin and bisepoxides are used under such conditions that they react only once with the agarose matrix and are therefore able to react with another reactant in step 2 and/or step 3. Higher order steps are possible but generally not necessary.

Generally speaking, the substituent in the derivatized agarose is attached to the agarose molecule through the oxygen atom from a hydroxyl group on the disaccharide unit, such substituents being connected to the disaccharide via ester, ether, amide, amine, isourea and carbamate linkages. To a lesser extent, other oxygen containing groups either initially present or introduced into the agarose molecule can provide reactive sites for attachment of the substituent. Examples of illustrative substituents are set forth in Table I.

In addition to their sieving properties, the derivatized agarose gels of the invention exhibit the following additional desirable features:

(1) No residual neurotoxins or other chemical hazards remaining in the formed gels,
(2) Gel clarity which is essentially equivalent to its polyacrylamide gel counterpart and substantially better than a corresponding underivatized agarose or starch gel,
(3) Sieving characteristics equivalent to polyacrylamide gels for proteins and other biological materials having molecular weights below 500,000 daltons,
(4) The ability to be used preparatively by the remelting or freeze-thaw recovery of separated proteins from the gel without extraneous contamination, and
(5) The ability to separate complex biological mixtures by the simultaneous application of sieving and/or hydrophobic, ion exchange, or biological affinity interactions. Manifestly, the derivatized agarose of the invention constitutes an advance over the sieving gels heretofore.

The invention is illustrated by the following examples.

Separation of Biological Substances by Electrophoresis using the Derivatized Agarose Sieving Gels of the Invention Example 1

The purpose of this example is to compare the sieving properties of a derivatized agarose of the invention with unmodified agarose. Thus, a gel consisting of 1% agarose derived from gracilaria agar and a tris (hydroxymethyl) aminomethane/sodium acetate buffer (0.04 M) containing 0.002 M ethylenediamine tetraacetic acid disodium salt was poured into an electrophoresis chamber which operated in a horizontal mode. Twelve lanes (or troughs) 10 MM wide were cut from the agarose slab, filled with a 1% solution of each of the different test agaroses and subsequently allowed to gel at room temperature. The test agaroses included those derived from both gelidium and gracilaria agar as well as a hydroxyethylated agarose of the invention which was prepared from a gelidium-derived agarose. The center sample well in each lane was loaded with 10 $\mu$l of ECO RI restricted lambda DNA solution. Electrophoresis was performed for 17 hours with ethidium bromide (0.5 $\mu$g/ml) and the bands photographed. The electrophoretic movement of the 6 characteristic DNA fragments present in the digest were retarded by approximately 50% in the hydroxyethylated agarose by comparison to any of the other agaroses. In addition, the electrophoretic pattern was compressed and the bands sharpened in the derivatized agarose gel. These effects clearly demonstrate the sieving characteristics of the agarose gels of the invention.

The hydroxyethylated agarose described above was obtained by reacting agarose with ethylene oxide in an alkaline medium and recovering the hydroxyethylated agarose product from the reaction mixture. The details of the reaction are given in U.S. Pat. No. 3,956,273 to Guiseley.

Example 2

A 4% (W/V) dispersion of a derivatized agarose having a 9% hydroxyethyl composition was heated to boiling until dissolved. The resultant sol was cooled to 75° C. and pipetted into a gel plate casting assembly consisting of 2 glass plates (10 cm×10 cm) and a 2 mm plastic, U-shaped spacer and several metal clamps to hold the glass plates securely on either side of the plastic spacer. Before the agarose sol was allowed to cool, a plastic sample comb, containing five 1 cm-wide teeth, was inserted into the top of the gel assembly. After gelation, the sample comb was removed along with the metal clamps and the 3 lower sides of the assembly were secured with waterproof plastic tape. The gel plate was then inserted in the rubber Grommet located in the upper reservoir of a standard vertical mode electrophoresis chamber.

An 80 μg/4 ml quantity of the sample proteins was applied in a buffered 40% sucrose solution to each sample slot. The pH 8.9 electrophoresis buffers (0.1 M) used contained in (hydroxymethyl) amino methane, ethylenediamine, tetraacetic acid disodium salt, and boric acid as described by Raymond et al. Anal. Biochem. 3,23 (1962). After electrophoresis of the sample proteins for 1 hour at 120 V, the gel was fixed in 10% sulfosalicylic acid, stained with Coomassie brilliant blue R-250 and destained in methanol:water:acetic acid (5:5:1).

Using this procedure it was possible to resolve the following proteins, having similar isoelectric points but different molecular weights, into the number of bands shown for each of the media listed in Table II. The data in the table clearly establish the enhanced sieving properties of the derivatized agarose gel of the invention.

Pore Size Determination of the Invention

The ultrastructure of 4% gels prepared from both underivatized agarose and agarose containing two levels of hydroxyethyl substitution was investigated by both transmission and scanning electron microscopy. The fixation and staining procedure involved the use of glutaraldehyde in cacodylate buffer followed by Osmium tetroxide infiltration, dehydration in an increasing series of alcohol titer, and final infiltration with an epoxide resin as described by ZVI Er El.

Under these conditions, the average pore diameter and standard deviation for each gel was found to vary as a function of hydroxyethyl substitution as shown in Table III.

TABLE I

**AGAROSE* DERIVATIVES FOR GEL SIEVING PROPERTIES**

| AGAROSE DERIVATIVE R = AGAROSE | DESIRABLE PROPERTIES |
|---|---|
| (1) R—OCH$_2$CHCH$_2$NH—CCH$_3$ with OH and =O | Sieving |
| (2) R—OCH$_2$CH$_2$NHCCH$_2$OH (with =O) | |
| (3) R—O—N (succinimide ring) | |
| (4) R—O— (cyclic acetal ring) | |
| (5) R—O—CH$_2$—C(=O)—NH—CH(CO$_2$H)—CH$_2$—(indole) | Sieving with some hydrophobic bonding |
| (6) R—O—P(Cl)(Cl) with dioxaphospholane-benzene | Sieving with some hydrophobic bonding |
| (7) R—O—CH$_2$CH$_2$—N (succinimide ring) | Sieving with some hydrophobic bonding |

TABLE I-continued
AGAROSE* DERIVATIVES FOR GEL SIEVING PROPERTIES

| AGAROSE DERIVATIVE R = AGAROSE | DESIRABLE PROPERTIES |
|---|---|
| (8) [pyranose sugar structure with R—O—CH₂, HO, OH, OH substituents], n = 1–10, Repeating monosacchride units: (Intra & intermolecular reaction) | Hydrophilic sieving galactose, glucose, mannose and/or gulose connected in 1,3; 1,4 and/or 1,6 glycosidic linkages |
| (9) [trisaccharide structure with R—O—CH₂... CH₂O—R— substituents], n = 1–10, monosacchrides as above | Hydrophilic sieving |
| (10) R—OCH₂CH₂—N[morpholine ring]O | Sieving and mild ion exchange prop.; anodal EEO |
| (11) R—O—[triazine with two NH₂ groups] | Sieving, ion exchange, anodal EEO control, DNA, RNA nucleotide separation |
| (12) R—O—[pyridine]—OCH₃ | Sieving: hydrophobic and mild ion exchange |
| (13) R—O—CH₂—[piperidine ring with N—CH₃] | Sieving; hydrophobic and mild ion exchange |
| (14) R—OCH₂CH₂—[purine/xanthine-like ring with two N—CH₃ groups and two C=O] | Selective separation of DNA, RNA and various nucleotides |
| (15) R—O—CH₂CH(OH)—CH₂—[phenyl with Cl] | Sieving and hydrophobic bonding |
| (16) R—O—[pyridine with CH₃ and HO substituents] | Sieving and hydrophobic mild ion exchange properties |

TABLE I-continued
AGAROSE* DERIVATIVES FOR GEL SIEVING PROPERTIES

| AGAROSE DERIVATIVE R = AGAROSE | DESIRABLE PROPERTIES |
|---|---|
| (17) R—O—CH$_2$—C$_6$H$_4$—CO$_2$H | Sieving and cation exchange properties |
| (18) R—O—CH$_2$—CH(OH)—CH$_2$—C$_6$H$_4$—CO$_2$H | Sieving and cation exchange properties |
| (19) R—O—CH$_2$—C$_6$H$_4$—SO$_3$H | Sieving and cation exchange properties |
| (20) R—O—CH$_2$—CH(OH)—CH$_2$—C$_6$H$_4$—SO$_3$H | Sieving with some hydrophobic bonding |
| (21) R—O—CH$_2$—C$_6$H$_3$(CO$_2$H)(CO$_2$H) | Sieving and cationic chelation |
| (22) R—CH$_2$CH$_2$—S(=O)—CH$_2$CH$_2$OH | Sieving and hydrophobic bonding |
| (23) R—O—CH$_2$—CH(—O—)CH$_2$ ; R—OCH$_2$—CHCH$_2$S$_2$O$_3^-$Na$^+$ (OH) ; R—OCH$_2$CHCH$_2$SH (OH) | Sieving and selective retention of proteins containing disulfide bonds or cysteine amino acids |
| (24) R—OCH$_2$CH(SH)CH$_2$OCH$_3$ | Sieving and selective retention of proteins containing disulfide bonds or cysteine amino acids |
| (25) R—[O—CH$_2$CH$_2$NH—C(=O)—NHCH$_2$—CH$_2$—NH$_2$] ; EAC ; R—O—EAC—GLU—P or GLU = glutaraldehyde P = Protein ; R—O—EAC—GLU—E or E = enzyme ; R—O—EAC—GLU—L L = lectin | Sieving plus special biological affinity sugar moiety selectivity and/or substrate specificity |

TABLE I-continued
AGAROSE* DERIVATIVES FOR GEL SIEVING PROPERTIES

| AGAROSE DERIVATIVE R = AGAROSE | DESIRABLE PROPERTIES |
|---|---|
| (26) R—O—C(=O)—NH—(CH$_2$)$_n$—NH—GLU—P<br>or GLU, P, E, L = as above<br><br>R—O—C(=O)—NH—(CH$_2$)$_n$—NH GLU—E<br>or<br><br>R—O—C(=O)—NH—(CH$_2$)$_n$—NH—GLU—L<br>n = 2–6 | Sieving plus special biological affinity sugar moiety selectivity and/ or substrate specificity |
| (27) R—NH(CH$_2$)$_n$—NH—P<br>n = 2–6<br>E or L can substitute for P | Sieving and special biological affinity, sugar moiety selectivity and/ or substrate specificity |
| (28) R—O—CH$_2$ C(=O)—NH—P<br>E or L can substitute for P | Sieving and special etc. as above |
| (29) R—O—CH—CONH$_2$<br>        |<br>    [CH—CONH$_2$]$_n$<br><br>n = 1–2000 | Sieving |

TABLE II
Relative Resolving Power of Various Electrophoretic Gel Sieving Media

| Gel Composition | Conc. (%) | Resolution (No.# of Protein Bands) | | | |
|---|---|---|---|---|---|
| | | Protein A | Protein B | Protein C | Protein D |
| Gelidium-derived Agarose | 4.0 | 2 | 1 | 4 | 2 |
| Gelidium-derived Agarose containing 9.0% hydroxyethylation | 4.0 | 4 | 3 | 5 | 4 |
| Polyacrylamide | 5.0 | 2 | 1 | 3 | 1 |
| Polyacrylamide | 7.5 | 5 | 5 | 2 | 4 |

| Protein Code | Identification |
|---|---|
| A | Ovalbumin (MW = 43,000; pI = 4.7) |
| B | Bovine serum albumin (MW = 67,000; pI = 4.7) |
| C | Ferritin (MW = 440,000; pI = 4.5) |
| D | Thyroglobulin (MW = 669,000; pI = 4.5) |

Note:
Many of the above proteins contain subunits or otherwise display microheterogeneity

TABLE III
Agarose Gel Pore Size Reduction by Derivatization

| Genus from which the agarose was derived | Wt. % of Derivative | Gel Conc. | Average pore diameter ± standard deviation (Mµ) |
|---|---|---|---|
| (1) Gelidium | 0 | 4% | 106 ± 52 |
| (2) Gelidium | 4 | 4% | 69 ± 52 |
| (3) Gelidium | 9 | 4% | 42 ± 18 |

What is claimed is:

1. A method of separating biological mixtures by subjecting them to gel electrophoresis using as the gel matrix a derivatized agarose containing at least one substituent having a preselected conformational shape such that the pore diameter of the derivatized agarose is not reduced below about 10° A units, the D.S. being from about 0.001 to about 2.0, whereby the components in said mixture are separated as a function of their molecular size.

2. The method according to claim 1 wherein the substituent is 2-hydroxyethyl.

3. The method according to claim 1 wherein the biological mixtures are DNA fragments.

4. The method according to claim 1 wherein the biological mixtures are proteins.

5. A derivatized agarose, useful as an electrophoretic sieving gel, containing at least one substituent having a molecular weight range greater than 100 to about 1,000,000 and a preselected conformational shape such that the average pore diameter of the derivatized agarose is not reduced below about 10° A units, the D.S. being from about 0.001 to about 2.0.

6. The derivatized agarose according to claim 5 wherein the substituent is attached to the agarose molecule via a linkage selected from the class consisting of ether, ester, amide, amine, isourea, and carbamate linkages.

7. The derivatized agarose according to claim 6 wherein the substituent is attached to the agarose molecule via an ether linkage.

8. The derivatized agarose according to claim 6 wherein the substituent is attached to the agarose molecule via an ester linkage.

9. The derivatized agarose according to claim 6 wherein the substituent is attached to the agarose molecule via an amide linkage.

10. The derivatized agarose according to claim 6 wherein the substituent is attached to the agarose molecule via an amine linkage.

11. The derivatized agarose according to claim 6 wherein the substituent is attached to the agarose molecule via an isourea linkage.

12. The derivatized agarose according to claim 6 wherein the substituent is attached to the agarose molecule via a carbamate linkage.

* * * * *